(12) United States Patent
Rehm et al.

(10) Patent No.: US 7,262,319 B2
(45) Date of Patent: Aug. 28, 2007

(54) PHENOLIC ANTIOXIDANTS IN CRYSTALLINE FORM

(75) Inventors: Daniel Rehm, March (DE); Johannes Schäfter, Lörrach (DE); Paul Adriaan Van Der Schaaf, Hagenthal-le-Haut (FR); Christian Guckel, Bad Säckingen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 225 days.

(21) Appl. No.: 10/534,513

(22) PCT Filed: Nov. 17, 2003

(86) PCT No.: PCT/EP03/50838

§ 371 (c)(1),
(2), (4) Date: May 11, 2005

(87) PCT Pub. No.: WO2004/048312

PCT Pub. Date: Jun. 10, 2005

(65) Prior Publication Data

US 2006/0189820 A1    Aug. 24, 2006

(30) Foreign Application Priority Data

Nov. 26, 2002    (EP) .................. 02406023

(51) Int. Cl.
*C07C 69/76*    (2006.01)
(52) U.S. Cl. .................. 560/75; 252/182.31; 252/397; 514/419
(58) Field of Classification Search .................. 560/75; 252/397, 182.31; 514/419
See application file for complete search history.

(56) References Cited

U.S. PATENT DOCUMENTS

| 3,543,293 A | 11/1970 | Akagi et al. ................ 260/562 |
| 3,644,482 A | 2/1972 | Dexter et al. ................ 260/473 |
| 3,666,809 A | 5/1972 | Okuno et al. ................ 260/561 |
| 4,683,326 A * | 7/1987 | Orban et al. .................. 560/75 |
| 4,708,979 A | 11/1987 | Pedrazzetti et al. ......... 524/249 |
| 4,847,585 A | 7/1989 | Kirilloff et al. ............... 560/75 |
| 5,212,222 A | 5/1993 | Mitsuuchi et al. .......... 524/230 |
| 6,375,977 B1 | 4/2002 | Auguste et al. ............. 424/447 |
| 6,740,694 B2 * | 5/2004 | von Frieling et al. ......... 524/94 |

FOREIGN PATENT DOCUMENTS

| AU | 288839 | 4/1967 |
| EP | 0498620 | 8/1992 |
| EP | 0562856 | 9/1993 |
| EP | 0563906 | 10/1993 |
| GB | 1327591 | 8/1973 |

OTHER PUBLICATIONS

Derwent Abstract 1988-224229 [32] for JP 63159315 (1988).

* cited by examiner

*Primary Examiner*—Thomas McKenzie
*Assistant Examiner*—Sudhakar Katakam
(74) *Attorney, Agent, or Firm*—Tyler A. Stevenson

(57) ABSTRACT

The invention relates to a process for preparing solid particles of a phenolic antioxidant from the IRGANOX series in the form of crystals, particularly IRGANOX 1010 and 1098, the crystal particles obtainable by the process, the further processing of the crystal particles, an aqueous dispersion comprising the phenolic antioxidant, novel crystal modifications of pentaerythritol tetrakis[3-(3,5-di-tert-butyl-4-hydroxyphenyl)-propionate] (μ-form) and N,N'-hexane-1,6diyl-bis[3-(3,5-di-tert-butyl-4-hydroxypheylpropamide)] (β-form) and aqueous dispersion comprising the new crystal modifications.

17 Claims, No Drawings

PHENOLIC ANTIOXIDANTS IN CRYSTALLINE FORM

The invention relates to a process for preparing solid particles comprising in essentially crystalline form a phenolic antioxidant, the solid particles obtainable by the process, the further processing of the solid particles, an aqueous dispersion comprising the phenolic antioxidant, a novel crystal modification (μ-form) of pentaerythritol tetrakis[3-(3,5-di-tert-butyl-4-hydroxyphenyl)-propionate], a novel crystal modification (β-form) of N,N'-hexane-1,6-diyl-bis [3-(3,5-di-tert-butyl-4-hydroxyphenylpropionamide)], aqueous dispersions comprising the crystal modifications and processes for preparing the crystal modifications.

Solid phenolic additives, such as certain commercial antioxidants from the Irganox® (trade mark of Ciba Specialty Chemicals) series, e.g. IRGANOX 1010: pentaerythritol tetrakis[3-(3,5-di-tert-butyl-4-hydroxyphenyl)-propionate], CAS No. 6683-19-8, or IRGANOX 1098: N,N'-hexane-1,6-diyl-bis[3-(3,5-di-tert-butyl-4-hydroxyphenylpropionamide)], CAS No. 23128-74-7, are used for a great variety of technical applications, e.g, for the stabilisation of polymers against oxidative, thermal or light induced degradation.

These additives are commercially distributed in the form of solid particles, e.g. powders, comminuted powders or granulates. The preparation of these particles from liquid reaction mixtures requires a separation step from the liquid phase.

The separation of solid particles obtained in crystal form from liquid reaction mixtures has certain drawbacks. The formation of crystalline particles in a liquid phase is a time consuming process that has to be carefully monitored with regard to the composition of the liquid phase, concentration and temperature.

The preparation of solid phenolic antioxidants, such as IRGANOX 1010 or 1098, from a melt phase, as opposed to a crystallisation process, has certain drawbacks. The melt phase of these products contains large amounts of amorphous particles. It has been found that amorphous particles of these phenolic antioxidants are subject to undesirable discolouration processes, the so-called greening. The explanation for this effect is the possible migration of oxygen in amorphous material. The crystal lattice of crystalline material would prevent the migration of oxygen.

Therefore, solid phenolic antioxidants, such as IRGANOX 1010 or 1098, are presently isolated in crystal form from the undesirable solvent methanol to exclude the formation of any amorphous material. Methanol is chosen in view of the fact that mixtures of crystalline and amorphous solids are obtained from other liquid mixtures. Discolouration is a problem even if residual amounts (less than 1%) of amorphous solids are present in crystalline solids.

There is a strong need for an improved alternative process that avoids the problems of the crystal formation process presently used for the preparation of solid phenolic antioxidants, such as IRGANOX 1010 or 1098.

It has surprisingly been found that the undesirable discolouration effect resulting from the formation of amorphous particles is avoided in the event that the particles of phenolic anti-oxidants are isolated from an aqueous phase to which a selected non-ionic surfactant and seed crystals have been added.

Therefore, the present invention relates to a process for preparing solid particles comprising in essentially crystalline form a compound of the formula:

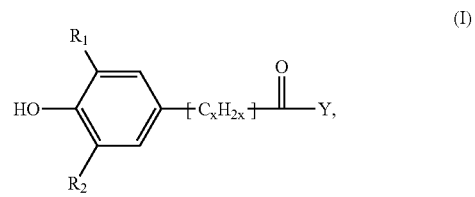

wherein one of $R_1$ and $R_2$ independently of one another represents hydrogen or $C_1$–$C_4$alkyl and the other one represents $C_3$–$C_4$alkyl;

x represents zero (direct bond) or a numeral from one to three; and

Y represents $C_8$–$C_{22}$alkoxy; or groups of the partial formulae

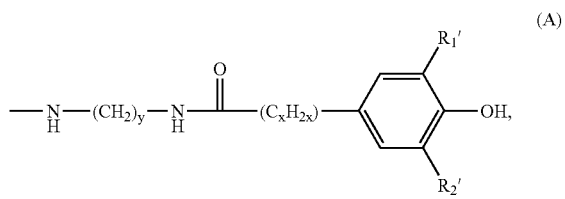

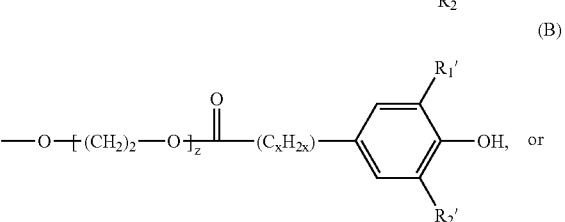

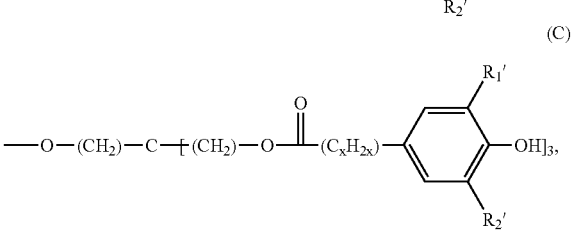

wherein one of $R_1'$ and $R_2'$ independently of one another represents hydrogen or $C_1$–$C_4$alkyl and the other one represents $C_3$–$C_4$alkyl;

x represents zero (direct bond) or a numeral from one to three;

y represents a numeral from two to ten; and z represents a numeral from two to six, which is characterised in that a homogeneous aqueous dispersion is prepared, which comprises the compound (I) or a mixture thereof, wherein $R_1$, $R_2$, $R_1'$, $R_2'$, Y, x, y and z are as defined above, crystals are formed by the addition of a fatty acid partial ester of polyoxyethylene sorbitan and seed crystals and the crystals obtained are separated from the dispersion.

A preferred embodiment of the invention relates to a process for preparing solid particles comprising in essentially crystalline form a compound (I) or a mixture thereof, wherein one of $R_1$ and $R_2$ independently of one another represents hydrogen or tert-butyl and the other one represents tert-butyl;

x represents two; and

Y represents $C_8$–$C_{22}$alkoxy; or groups of the partial formulae (A), (B) or (C), wherein one of $R_1'$ and $R_2'$ independently of one another represents hydrogen or tert-butyl and the other one represents tert-butyl;

x represents two; y represents six; and z represents three, which is characterised in that the crystals are formed by the addition of polyoxyethylene-(20 or 5)-sorbitan monooleate.

The general terms used in the description of the instant invention, unless defined otherwise, are defined as follows:

The term solid particle form defines any aggregates or agglomerates of solid particulate matter, such as powders, crystals, comminuted crystals or granulates prepared from crystals and the like.

The term crystalline form defines any solid matter, wherein the molecules are arranged in a geometrically regular pattern, as opposed to amorphous forms.

The term in essentially crystalline form defines the exclusion of substantial amounts of amorphous particles from any compositions or agglomerates of crystalline particles. In a preferred embodiment of the invention less than 1% of amorphous particles are present in crystal isolates. In a particularly preferred embodiment of the invention less than 0.5% of amorphous particles are present in crystal isolates.

In a compound of the formula (I) $R_1$ and $R_2$ defined as $C_1$–$C_4$alkyl comprise the unbranched and branched (where possible) groups methyl, ethyl, n-propyl, isopropyl, n-butyl, isobutyl and tert-butyl.

$R_1$ and $R_2$ defined as $C_3$–$C_4$alkyl comprises unbranched and preferably branched groups, e.g. isopropyl, isobutyl or tert-butyl.

In a preferred embodiment of the invention one of $R_1$ and $R_2$ represents hydrogen or $C_1$–$C_4$alkyl, particularly methyl or tert-butyl, and the other one represents $C_3$–$C_4$alkyl, particularly tert-butyl.

In a compound (I) the index x represents zero (direct bond) or a numeral from one to three.

In the event that x is zero, the direct bond is defined.

In the event that x is one, the group —$[C_xH_{2x}]$— represents methylene.

In a preferred embodiment x represents two. In that case the group —$[C_xH_{2x}]$— represents 1,1- or preferably 1,2-ethylene.

In the event that x represents the numeral three, the group —$[C_xH_{2x}]$— represents 1,1-, 1,2- or preferably 1,3-propylene.

Y defined as $C_8$–$C_{22}$alkoxy represents, for example n-octyloxy, 2-ethylhexyloxy, 1,1,3,3-tetramethylbutoxy, 1-methylheptyloxy, n-nonyloxy or 1,1,3-trimethylhexyloxy or $C_{10}$–$C_{22}$-alkoxy, particularly straight chained $C_{10}$–$C_{22}$alkoxy, e.g. n-decyloxy, n-dodecyloxy n-tetradecyloxy, n-hexadecyloxy or n-octadecyloxy or higher homologues thereof.

In the groups of the partial formulae (A), (B) and (C) $R_1'$ and $R_2'$ defined as $C_1$–$C_4$alkyl are identical with $R_1$ and $R_2$ defined above.

In a group of the partial formula (A) x represents zero (direct bond) or a numeral from one to three and y represents a numeral from two to ten. In a preferred embodiment x represents two and y represents six.

In a group of the partial formula (B) x represents zero (direct bond) or a numeral from one to three and z represents a numeral from two to ten. In a preferred embodiment x represents two and z represents three.

In a group of the partial formula (C) x represents zero (direct bond) or a numeral from one to three and z represents a numeral from two to ten. In a preferred embodiment x represents two.

A particularly preferred compound (I), wherein Y represents a group of the partial formula (A), one of $R_1$ and $R_2$ and correspondingly one of $R_1'$ and $R_2'$ represents methyl and the other one represents tert-butyl, x represents two and y represents six, is IRGANOX 1098: N,N'-hexane-1,6-diyl-bis[3-(3,5-di-tert-butyl-4-hydroxyphenylpropionamide)].

A particularly preferred compound (I), wherein Y represents a group of the partial formula (B), one of $R_1$ and $R_2$ and correspondingly one of $R_1'$ and $R_2'$ represents methyl and the other one represents tert-butyl, x represents two and z represents three, is IRGANOX 245: ethylene-bis(oxyethylene)bis[3-(5-tert-butyl-4-hydroxy-m-tolyl)-propionate], CAS No. 36443-68-2.

A particularly preferred compound wherein Y represents a group of the partial formula (C), $R_1$ and $R_2$ and correspondingly $R_1'$ and $R_2'$ represent tert-butyl, is IRGANOX 1010: pentaerythritol tetrakis[3-(3,5-di-tert-butyl-4-hydroxyphenyl)-propionate].

The term aqueous dispersion comprises any mixture of two phases wherein dispersed particles are distributed in a dispersant phase (dispergens), which in the instant case is water.

The term homogeneous aqueous dispersion is defined within the limits of so-called liquid/liquid, e.g. emulsions, or solid/liquid disperse systems, e.g. suspensions, as opposed to other types of dispersions, such as solid/gas, e.g. fumes, or gas/liquid, e.g. foams, dispersions. Liquid/liquid dispersions are commonly defined as emulsions and consist of two separate liquid phases of different polarity. In the instant case a phase of non-polar character, obtained from a melt of the compound (I is dispersed in a polar phase, e.g. water.

In an alternative embodiment solid/liquid dispersions are commonly defined as suspensions. In the instant case, solid particles, e.g. seed crystals or amorphous particles of the compound (I), are dispersed in the polar phase, e.g. water or an aqueous alcoholic solution.

The mentioned partial fatty acid ester of polyoxyethylene sorbitan consists preferably of a substantially pure ester of sorbitan or a mixture of different esters of sorbitan, in which the structure of the fatty acid groups and the length of the polyoxyethylene chains vary. The sorbitan is preferably etherified by three polyoxyethylene chains and esterified by one fatty acid group. Alternatively, however, the sorbitan may be etherified by only one or two polyoxyethylene chains and accordingly esterified by two or three fatty acid groups. Altogether, the sorbitan base structure is substituted by a minimum of two and a maximum of four hydrophilic groups. The term hydrophilic group applies to the polyoxyethylene chains and the fatty acid groups.

The polyoxyethylene chain is straight-chained and has preferably from 4 to 10, especially from 4 to 8, ethylene oxide units. The ester groups on the sorbitan base structure are derived from a saturated or unsaturated, straight-chained carboxylic acid having an even number of from 8 to 20 carbon atoms. The ester group derived from that carboxylic acid is preferably straight-chained and has 12, 14, 16 or 18 carbon atoms, e.g. n-dodecanoyl, n-tetradecanoyl, n-hexadecanoyl or n-octadecanoyl. The ester group derived from an unsaturated carboxylic acid having an even number of from 8 to 20 carbon atoms is preferably straight chained and has 12, 14, 16 or 18 carbon atoms, e.g. oleoyl.

Suitable partial fatty add esters of polyoxyethylene sorbitan are available commercially under the trademark Tween® of ICI. According to a preferred embodiment of the process, the crystals are formed by the addition of a fatty acid partial ester of polyoxyethylene sorbitan selected from the group consisting of polyoxyethylene-(20 or 4)-sorbitan monolaurate (TWEEN 20 and 21), polyoxyethylene-(20)-sorbitan monopalmitate or monostearate (TWEEN 40 and 60), polyoxyethylene-(4 or 20)-sorbitan monostearate or tristearate (TWEEN 61 and 65), polyoxyethylene-(20 or 5)-sorbitan monooleate (TWEEN 80 or 81) and polyoxyethylene-(20)-sorbitan trioleate (TWEEN 85).

According to a preferred embodiment of the process the crystals are formed by the addition of polyoxyethylene-20 or 5)sorbitan monooleate.

The process for preparing the solid particles defined above is novel and inventive. In a first step an aqueous dispersion is prepared. The aqueous dispersion comprises
a) In essentially crystalline form a compound (I) or a mixture thereof, wherein $R_1$, $R_2$, $R_1'$, $R_2'$, Y, x, y and z are as defined above;
b) A fatty acid partial ester of polyoxyethylene sorbitan; and
c) Water.

The present invention also relates to the aqueous dispersion as defined above and to the process for preparing the dispersion.

A particularly preferred embodiment of the invention relates to the aqueous dispersion comprising as component a) in essentially crystalline form pentaerythritol tetrakis[3-(3,5-di-tert-butyl-4-hydroxyphenyl)-propionate].

Another particularly preferred embodiment of the invention relates to the aqueous dispersion comprising as component a) in essentially crystalline form N,N'-hexane-1,6-diyl-bis[3-3,5-di-tert-butyl hydroxyphenylpropionamide)].

According to the first step of the process, an emulsion of the o/w-type comprising the components a) within the aqueous phase is prepared. This emulsion is characterised by long storage stability.

According to an alternative embodiment, a suspension comprising the components a) within the aqueous phase is prepared. This aqueous suspension is characterised by long storage stability. The emulsion is prepared by heating a compound (I) or a mixture with other compounds (I) or other additives to temperatures, preferably between 80° C. and 200° C., to give a melt which is then dispersed in an aqueous dispersion comprising from 0.1 to 10.0% (by weight), preferably 0.1 to 5.0%, most preferably 0.5 to 1.0% fatty acid partial ester of polyoxyethylene sorbitan and preferably 0.1 to 10.0%, preferably 0.1 to 5.0% and most preferably 0.1 to 1.0% seed crystals.

The melt may also be obtained directly from the preceding process for the preparation of the compound (I). IRGANOX 1010 is obtained without the presence of a solvent by catalytic transesterification of methyl 3-(3,5-di-tert-butyl-4-hydroxyphenyl)-propionate with pentaerythritol and subsequent distillation of the melt in the vacuum at elevated temperatures.

The amount of water present in the aqueous dispersion to which the melt is added may vary within wide limits. A sufficient amount of water must be present to ensure the complete solubility of the melt phase in water. The maximum amount must permit crystallisation at the given temperature in sufficient yield. In a preferred embodiment water is present within the range from the equivalent weight amount 1:1 to the excess amount of 10:1.

The aqueous suspension is prepared by heating amorphous or crystalline seed particles of a particle size of about 1–50μ, preferably 5–50μ comprising a compound (I) or a mixture with other compounds (I) and other additives to temperatures, preferably between 80° C. and 90° C., and dispersing the seed particles in water comprising from 0.1 to 10.0% (by weight), preferably 0.1 to 5.0%, most preferably 0.5 to 1.0% fatty add partial ester of polyoxyethylene sorbitan and 1.0 to 50.00%, preferably 30 to 50.0% seed crystals.

The presence of a co-solvent is optional. Suitable co-solvents are water-soluble polar protic solvents, such as a lower alcohol selected from the group consisting of ethanol, isopropanol and 2-butanol.

The addition of water-soluble additives, such as sodium chloride or lithium acetate, is optional to improve the yield of the crystals obtained and to accelerate the rate of crystal formation by applying the so-called salting-out effect.

In a preferred embodiment of the invention the aqueous dispersion to which the melt or amorphous or crystalline seed particles are added comprises polyoxyethylene-(20 or 5)-sorbitan monooleate.

In a further preferred embodiment of the invention IRGANOX 1010 and IRGANOX 1098 are obtained from aqueous dispersions comprising a lower alcohol selected from the group consisting of ethanol, isopropanol and 2-butanol as co-solvents, to which polyoxyethylene-(20 or 5)-sorbitan monooleate is added. At temperatures above 90° C. the new crystal modifications (μ-form) of pentaerythritol tetrakis[3-(3,5-di-tert-butyl-4-hydroxyphenyl)propionate] and N,N'-hexane-1,6-diyl-bis[3-(3,5-di-tert-butyl-4-hydroxyphenyl-propionamide)] (β-form) are formed which are described in detail below.

The present invention also relates to a new crystal form, particularly the new crystal modification (μ-form), of pentaerythritol tetrakis[3-(3,5-di-tert-butyl-4-hydroxyphenyl)-propionate] and mixtures of this new crystal modification with other crystal modifications, such as the ones described in U.S. Pat. No. 4,683,326.

The present invention also relates to a new crystal form, particularly the new crystal modification (β-form), of N,N'-hexane-1,6-diyl-bis[3-(3,5-di-tert-butyl-4-hydroxyphenyl-propionamide)] and mixtures of this new crystal modification with other crystal modifications obtainable by known methods.

In an alternative embodiment the melt or amorphous or crystalline seed particles of the compound (I) or a mixture with other compounds (I) or other additives are added to water to which the fatty acid partial ester of polyoxyethylene sorbitan is added to give an emulsion or suspension comprising the same percent weight amounts of the components a) and b).

The dispersion is made homogeneous by conventional mixing methods, such as the ones known for preparing emulsions or suspensions. Mixing is effected thoroughly throughout the dispersion by vigorous shaking using a dispersing machine, for example a Vortex mixer, or using dispersing machines of the ®POLYTRON type (Kinematica AG, Littau Switzerland) or dispersing machines produced by IKA (Staufen Germany), a static mixer and conventional stirring machines having a propeller, anchor or paddle blade or using a phase mixer.

In order to obtain an especially homogeneous mixture, stirring is carried out at high speed, for example using Y-beam agitators (®Y-Strahl, ®Ultraturrax) or stirring machines produced by Polytron, for example Polytron PT 3000 or DH 30/30 or using high pressure rotor/stator mixer, for example the BUSS mixing turbine.

Subsequent crystallisation is carried out, if desired, by inoculating the emulsion with suitable crystal seeds. In a preferred embodiment of the process the seed crystals are identical with the compound (I) or a mixture thereof forming the melt and the subsequent emulsion.

In the event that the homogenous dispersion is prepared from a suspension, the seed crystals are identical with the compound (I) or a mixture thereof forming the suspension.

The time period needed for forming the crystals may vary within wide limits and depends on a batch-wise or continuous process procedure. In a batch process a suitable time period is from 1 to 60 min., preferably from 10 to 60 min. and most preferably from 10 to 30 minutes.

The crystals formed by the process are almost 100% crystalline and virtually free of amorphous particles. Crystalline isolates, such as granulates, meet stringent quality requirements with regard to light stability.

The crystals present in the aqueous dispersion are subsequently separated from the aqueous dispersion and may be subsequently dried, and, if desired, converted to smaller particles sizes by conventional grinding methods, such as wet grinding with a ball mill. This prevents the inclusion of air or other undesirable particles.

The separation from the aqueous dispersion includes the application of any state of the art method known for separating binary solid/liquid mixtures, e.g. filtration, centrifugation or decantation. To remove any impurity the crystalline residue may be purified by the addition of water or an aqueous solution containing the above-mentioned alcohols and subsequently dried by applying the known drying techniques, particularly by applying reduced pressure or a vacuum at elevated temperatures up to 100° C.

A further embodiment of the invention relates to the subsequent process step of further processing the solid particles comprising in essentially crystalline form the compound (I), which is characterised in that a homogeneous aqueous dispersion is prepared, which comprises the compound (I) or a mixture thereof, wherein $R_1$, $R_2$, $R_1'$, $R_2'$, Y, x, y and z are as defined above, crystals are formed by the addition of a fatty acid partial ester of polyoxyethylene sorbitan and seed crystals and the crystals obtained are separated from the dispersion and further processed to other solid particle forms.

According to a preferred embodiment of the process the crystals obtained are separated from the dispersion and converted to granulates.

The term solid particles also defines further processed compressed particle forms, to which pressure has been applied when forming the particles from solid aggregates or agglomerates.

The compressed articles, such as granulates, comprising a compound (I) or a mixture thereof in essentially crystalline form obtainable by the process as defined above are also subject matter of the present invention.

Compressed particle forms are obtained by applying conventional machinery, such as internal mixers, extruders, e.g. single or twin screw extruders or planetary roller extruders, or kneaders. If an internal mixer or extruder is employed, the process is preferably carried out continuously, whereas in a kneader the process is preferably carried out batch-wise. The dried comprimates obtained, e.g. the extrudates, may then be reduced to the desired particle sizes by applying conventional grinding or milling techniques.

The term compressed particle forms particularly relates to further processed granulates formed from powders or any other fine particles by applying conventional granulation methods, such as wet granulation or compaction.

Many methods are known for the manufacture of granules and related agglomerates. Granules may be formed from powders and other fine particles by suitable agitation in the presence of a suitable binding liquid, such as water. Granules may also be formed from powders by pressurized compaction and extrusion methods by applying pressure. Application of heat to the powder may result in the sintering and formation of agglomerates of suitable size. Drying and solidification on surfaces may also produce granular products. Solutions, suspensions or melts are applied to a heated or cooled surface, and the solids are scraped off. In spray-drying, a pumpable and dispersible feed liquid, which may be a solution, gel, paste, emulsion, slurry or melt, is sprayed into a chamber, wherein solidification occurs. The chamber is heated to evaporate the solubilising or emulsifying liquid, or cooled down to allow the solidification of a melt.

The solid particle forms, or, in the alternative, the aqueous dispersion from which the solid particle forms are prepared, or the compressed particle forms defined above optionally comprise additional additives, so-called blends, suitable for use in polymers, preferably additives customarily used for improving the chemical and physical properties of polymers containing these additives. The auxiliaries can be present in varying proportions, for example, in amounts of up to 40.0% by weight, preferably from 0.05% to 40.0% by weight, more preferably from 0.05% to 25.0% by weight, with particular preference from 0.05% to 10.0% by weight based on the total weight of the composition. Suitable groups of additional additives are listed up here by way of example: antioxidants selected from the group consisting of alkylated monophenols, alkylthiomethylphenols, hydroquinones and alkylated hydroquinones, tocopherols, hydroxylated thiodiphenyl ethers, alkylidene-bis-phenols, O-, N- and S-benzyl compounds, hydroxybenzylated malonates, aromatic hydroxybenzyl compounds, triazine compounds, benzylphosphonates, acylaminophenols, esters and amides of β-(3,5-di-t-butyl-hydroxyphenyl)propionic acid, β-(3,5-di-t-butyl-4-hydroxy-3-methylphenyl)propionic acid, or β-(3,5-dicyclohexyl-4-hydroxyphenyl)propionic acid, ascorbic acid, aminic antioxidants, light stabilisers, phosphates, phosphines, phosponites, hydroxylamines, nitrones, thiosynergists, peroxide scavengers, polyamide stabilisers, basic co-stabilisers, nucleating agents, fillers and reinforcing agents, plasticisers, lubricants, emulsifiers, pigments, rheological additives, levelling assistants, optical brighteners, flame proofing agents, antistatic agents, blowing agents, benzofuranones and indolinones.

Suitable additives optionally present in the aqueous dispersion according to the present invention may be selected from the following non-exhaustive list of specific additives:

1. Antioxidants
1.1 Alkylated monophenols, for example 2,6-di-t-butyl-4-methylphenol, 2-butyl-4,6-di-methylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, linear or side chain-branched nonylphenols; such as 2,6-di-nonyl-methylphenol, 2,4-dimethyl-6-(1-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2 Alkylthiomethylphenols, for example 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol.

1.3 Hydroquinones and alkylated hydroquinones, for example 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyanisole, 3,5-di-t-butyl-4-hydroxyphenyl stearate, bis(3,5-di-t-butyl-4-hydroxyphenyl) adipate.

1.4 Tocopherols, for example α-, β, γ- or δ-tocopherols and mixtures thereof (vitamin E).

1.5 Hydroxylated thiodiphenyl ethers, for example 2,2'-thiobis(6-t-butyl-4-methylphenol), 2,2'-thio-bis(4-octylphenol), 4,4'-thiobis(6-t-butyl-3-methylphenol), 4,4'-thiobis(6-t-butyl-2-methylphenol), 4,4'-thio-bis(3,6-di-sec-amylphenol), 4,4'-bis(2,6-dimethyl hydroxyphenyl) disulphide.

1.6 Alkylidene-bis-phenols, for example 2,2'-methylene-bis(6-t-butyl-4-methylphenol), 2,2'-methylene-bis(6-t-butyl-4-ethylphenol), 2,2'-methylene-bis[4-methyl-6-(-methylcyclohexyl)phenol], 2,2'-methylene-bis(4-methyl-6-cyclohexylphenol), 2,2'-methylene-bis(6-nonyl-4-methylphenol), 2,2'-methylene-bis(4,6-di-t-butylphenol), 2,2'-ethylidene-bis(4,6-di-t-butylphenol), 2,2'-ethylidene-bis(6-t-butyl-4-isobutylphenol), 2,2'-methylene-bis[6-(α-methylbenzyl)4-nonylphenol], 2,2'-methylene-bis[6-(α,α-dimethylbenzyl)-4-nonylphenol], 4,4'-methylene-bis(2,6-di-t-butylphenol), 4,4'-methylene-bis(6-t-butyl-2-methylphenol), 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl-3-n-dodecylmercaptobutane, ethylene glycol-bis[3,3-bis(3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra-(5-t-butyl-4-hydroxy-2-methylphenyl)pentane.

1.7 O-, N- and S-benzyl compounds, for example 3,5,3',5'-tetra-t-butyl-4,4'-dihydroxydibenzyl ether, octadecyl 4-hydroxy-3,5-dimethylbenzylmercaptoacetate, tridecyl 4-hydroxy-3,5-di-t-butylbenzylmercaptoacetate, tris(3,5-di-t-butyl-4-hydroxybenzylamine, bis(4-t-butyl-3-hydroxy-2,6-dimethylbenzyl)-dithioterephthalate, bis(3,5-di-t-butyl-4-hydroxybenzyl)-sulphide, isooctyl 3,5-di-t-butyl-4-hydroxybenzylmercaptoacetate.

1.8 Hydroxybenzylated malonates, for example dioctadecyl 2,2-bis(3,5-di-t-butyl-2-hydroxybenzyl)malonate, dioctadecyl 2-(3-t-butyl-4-hydroxy-5-methylbenzyl)malonate, didodecyl mercaptoethyl-2,2-bis(3,5-di-t-butyl-4-hydroxybenzyl)malonate, di-[4-(1,1,3,3-tetramethylbutyl)phenyl]-2,2-bis(3,5-di-t-butyl-4-hydroxybenzyl)malonate.

1.9 Aromatic hydroxybenzyl compounds, for example 1,3,5-tris(3,5-di-t-butyl-4-hydroxybenzyl)-2,4,6-trimethylbenzene, 1,4-bis(3,5-di-t-butyl-4-hydroxybenzyl)-2,3,5,6-tetramethylbenzene, 2,4,6-tris(3,5-di-t-butyl-4-hydroxybenzyl)phenol.

1.10 Triazine compounds, for example 2,4-bisoctylmercapto-6-(3,5-di-t-butyl-4-hydroxyanilino)-1,3,5-triazine, 2-octylmercapto-4,6-bis(3,5-di-t-butyl-4 hydroxyanilino)-1,3,5-triazine, 2-octylmercapto-4,6-bis(3,5-di-t-butyl-4-hydroxyphenoxy)-1,3,5-triazine, 2,4,6-tris(3,5-di-t-butyl-4-hydroxyphenoxy)-1,2,3-triazine, 1,3,5-tris(3,5-di-t-butyl-4-hydroxybenzyl)-isocyanurate, 1,3,5-tris(4-t-butyl-3-hydroxy-2,6-dimethylbenzyl)-isocyanurate, 2,4,6-tris(3,5-di-t-butyl-4-hydroxyphenylethyl)-1,3,5-triazine, 1,3,5-tris(3,5-di-t-butyl-4-hydroxyphenylpropionyl)-hexahydro-1,3,5-triazine, 1,3,5-tris(3,5-dicyclohexyl-4-hydroxybenzyl)-isocyanurate.

1.11 Benzylphosphonates, for example dimethyl 2,5-di-t-butyl-4-hydroxybenzyl-phosphonate, diethyl 3,5-di-t-butyl-4-hydroxybenzylphosphonate, dioctadecyl 3,5-di-t-butyl-4-hydroxybenzylphosphonate, dioctadecyl 5-t-butyl-4-hydroxy-3-methylbenzylphosphonate, the calcium salt of the monoethyl ester of 3,5-di-t-butyl-4-hydroxybenzylphosphonic acid.

1.12 Acylaminophenols, for example 4-hydroxylauranilide, 4-hydroxystearanilide, octyl N-(3,5-di-t-butyl-4-hydroxyphenyl)carbamate.

1.13 Esters of β-(3,5-di-t-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (2-hydroxyethyl)isocyanurate, N,N'-bis(2-hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(5-t-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(2-hydroxyethyl)-isocyanurate, N,N'-bis(2-hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(2-hydroxyethyl)-isocyanurate, N,N'-bis(2-hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,5-di-t-butyl-4-hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(2-hydroxyethyl)-isocyanurate, N,N'-bis(2-hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-t-butyl-4-hydroxyphenyl)propionic add e.g. N,N'-bis(3,5-di-t-butyl-4-hydroxyphenylpropionyl)hexamethylenediamide, N,N'-bis(3,5-di-t-butyl-4-hydroxyphenylpropionyl)trimethylenediamide, N,N'-bis(3,5-di-t-butyl-4-hydroxyphenylpropionyl)-hydrazide, N,N'-bis[2-(3-[3,5-di-t-butyl-4-hydroxyphenyl]propionyloxy)ethyl]-oxamide (Naugard® XL-1 from Uniroyal).

1.18 Ascorbic acid (vitamin C).
1.19 Aminic antioxidants, for example N,N'-diisopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-t-octylphenyl)-1-naphthylamine, N-phenyl-2-naphthylamine, octylated diphenylamine, for example p,p'-di-t-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-t-butyl dimethylaminomethylphenol, 2,4'-diaminodiphenylmethane, 4,4'-diaminodiphenylmethane, N,N,N',N'-tetramethyl-4,4'-diamino-diphenylmethane, 1,2-di[(2-methylphenyl)amino]ethane, 1,2-diphenylaminopropane, (o-tolyl)biguanide, di-[4-(1',3'-dimethylbutyl)phenyl]amine, t-octylated N-phenyl-1-naphthylamine, a mixture of mono- and dialkylated t-butyl/t-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, mixtures of mono- and dialkylated t-butyldiphenylamines, 2,3-dihydro-3,3-dimethyl-4H-1,4-benzothiazine, phenothiazine, a mixture of mono- and dialkylated t-butyl/t-octyl-phenothiazines, a mixture of mono- and dialkylated t-octyl-phenothiazines, N-allylphenothiazine, N,N,N',N'-tetraphenyl-1,4-diaminobut-2-ene, N,N-bis(2,2,6,6-tetramethylpiperidin-4-yl) hexamethylenediamine, bis(2,2,6,6-tetramethylpiperidin-4-yl)sebacate, 2,2,6,6-tetramethylpiperidin-4-one and 2,2,6,6-tetramethylpiperidin-4-ol.
1.20 Polyphenolic antioxidants, for example derivates of p-cresol and dicyclopentadiene for example ®WINGSTAY L (Goodyear), CAS-No. 68610-51-5.

2. UV-absorbers and light stabilisers 2.1 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(,-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; R—CH$_2$CH$_2$—COO—CH$_2$CH$_2$—]$_2$, wherein R represents 3'-tert-butyl-4'-hydroxy-5'-2H-benzotriazol-2-ylphenyl, 2-[2'-hydroxy-3'-(dimethylbenzyl)-5'-(1,1,3,3-tetramethylbutyl)phenyl]benzotriazole; 2-[2'-hydroxy-3'-(1,1,3,3-tetramethylbutyl)-5'-(,-dimethylbenzyl)phenyl]benzotriazole.

2.2 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3 Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4 Acrylates, for example ethyl α-cyano-β, β-diphenyl acrylate or isooctyl α-cyano-β,β-diphenyl acrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(α-carbomethoxy-β-cyanovinyl)-2-methylindoline.

2.5 Nickel compounds, for example nickel complexes of 2,2'-thio-bis[4-(1,1,3,3-tetramethylbutyl)phenol], such as the 1:1- or 1:2-complex, with or without additional ligands, such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-t-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6 Sterically hindered amines, for example bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl) sebacate, bis(1-octyloxy-2,2,6,6-tetramethylpiperidin-4-yl)sebacate, bis(1,2,2,6,6-pentamethylpiperidyl)n-butyl-3,5-di-t-butyl-4-hydroxybenzylmalonate, the condensate of 1-hydroxyethyl-2,2,6,6-tetramethyl-4-hydroxypiperidine and succinic add, the linear or cyclic condensates of N,N'-bis(2,2,6,6-tetramethyl-4-piperidyl)hexamethylenediamine and 4-t-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-t-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the linear or cyclic condensates of N,N'-bis(2,2,6,6-tetramethyl-4-piperidyl) hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-piperidyl)-hexamethylenediamine and 4-cyclohexylamino-2,6-dichloro-1,3,5-triazine, the condensate of 1,2-bis(3-aminopropylamino) ethane and 2,4,6-trichloro-1,3,5-triazine and also 4-butylamino-2,2,6,6-tetramethylpiperidine (CAS No. 136504-96-6); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane, the reaction product of 7,7,9,9-tetramethyl-2-cycloundecyl-1-oxa-3,8-diaza-4-oxospiro[4.5]decane and epichlorohydrine, 1,1-bis(1,2,2,6,6-pentamethyl-4-piperidyloxycarbonyl)-2-(4-methoxyphenyl)ether, N,N'-bis-formyl-N,N'-bis(2,2,6,6-tetramethyl-4-piperidyl)-hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine.

2.7 Oxalamides, for example 4,4'-dioctyloxyoxanilide, 2,2'-diethoxy-oxanilide, 2,2'-dioctyloxy-5,5'-di-t-butyloxanilide, 2,2'-didodecyloxy-5,5'-di-t-butyloxanilide, 2-ethoxy-2'-ethyloxanilide, N,N'-bis(3-dimethylaminopropyl) oxalamide, 2-ethoxy-5-t-butyl-2'-ethyloxanilide and its mixture with 2-ethoxy-2'-ethyl-5,4'-di-t-butyloxanilide and mixtures of o- and p-methoxy- and of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6 -bis(2,4-dimethylphenyl)-1,3,5-triazine.

3. Metal deactivators, for example, N,N'-diphenyloxalamide, N-salicylal-N'-salicyloyl hydrazine, N,N'-bis(salicyloyl)hydrazine, N,N'-bis(3,5-di-t-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites, phosphines and phosphonites, for example triphenyl phosphite, diphenyl alkyl phosphites, phenyl dialkyl phosphites, tris(nonylphenyl) phosphite, trilauryl phosphite, trioctadecyl phosphite, trimethylphosphine, tri-n-butylphosphine, triphenylphosphine, distearyl pentaerythritol diphosphite, tris(2,4-di-t-butylphenyl) phosphite, diisodecyl pentaerythritol diphosphite, bis(2,4-di-t-butylphenyl)pentaerythritol diphosphite, bis(2,6-di-t-butyl-4-methylphenyl)pentaerythritol diphosphite, bisisodecyloxypentaerythritol diphosphite, bis(2,4-di-t-butyl-6-methylphenyl)pentaerythritol diphosphite, bis(2,4,6-tri-t-butylphenyl)pentaerythritol diphosphite, tristearyl sorbitol triphosphite, tetrakis(2,4-di-t-butylphenyl) 4,4'-biphenylene diphosphonite, 6-isooctyloxy-2,4,8,10-tetra-t-butyl-12H-dibenzo[d,g]-1,3,2-dioxaphosphocin, 6-fluoro-2,4,8,10-tetra-t-butyl-12-methyldibenzo[d,g]-1,3,2-dioxaphosphocin, bis(2,4-di-t-butyl-6-methylphenyl)methyl phosphite, bis(2,4-di-t-butyl-6-methylphenyl) ethyl phosphite, 2,2',2"-nitrilo[triethyltris-(3,3',5,5"tetra-t-butyl-1,1'-biphenyl-2,2'-diyl) phosphite], 2-ethylhexyl (3,3',5,5'-tetra-t-butyl-1,1'-biphenyl-2,2'-diyl) phosphite.

Particular preference is given to using the following phosphites:
tris(2,4-Di-t-butylphenyl) phosphite (Irgafos®168, Ciba Specialty Chemicals), tris(nonylphenyl) phosphite and the phosphites selected from the group comprising the structural formulae (a), (b), (c), (d), (e), (f) and (g) mentioned below:

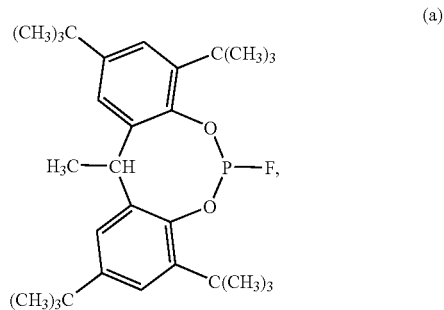

(a)

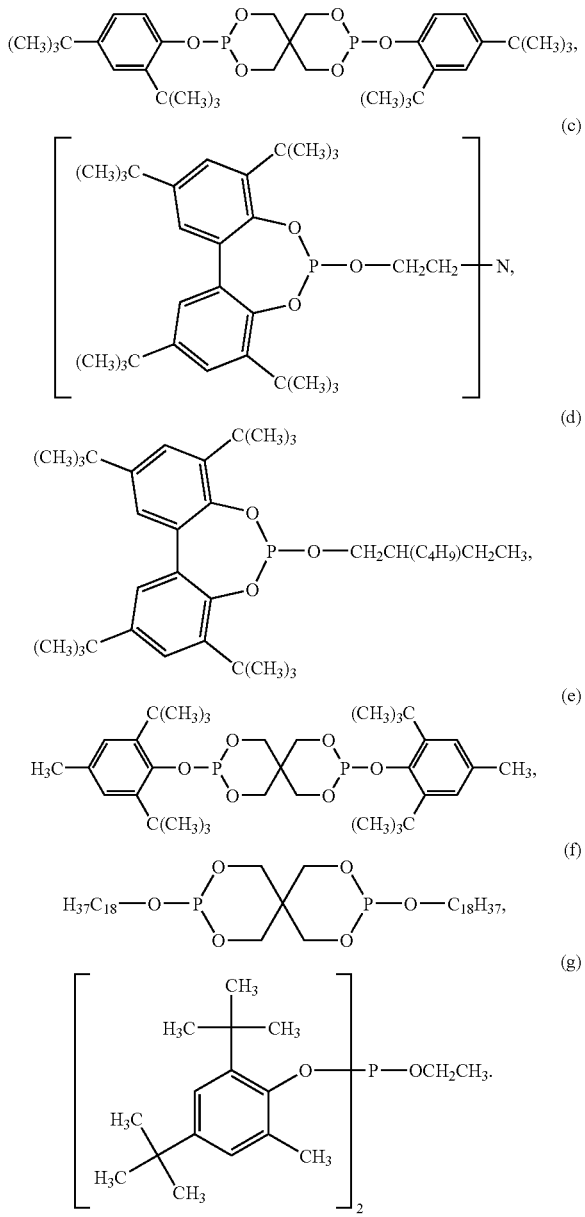

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl α-phenyl nitrone, N-ethyl α-methyl nitrone, N-octyl α-heptyl nitrone, N-lauryl α-undecyl nitrone, N-tetradecyl α-tridecyl nitrone, N-hexadecyl α-pentadecyl nitrone, N-octadecyl α-heptadecyl nitrone, N-hexadecyl α-heptadecyl nitrone, N-octadecyl α-pentadecyl nitrone, N-heptadecyl α-heptadecyl nitrone, N-octadecyl α-hexadecyl-nitrone, and nitrones derived from N,N-dialkylhydroxylamines prepared from hydrogenated tallow fatty amines.

7. Thiosynergists, for example dilauryl or distearyl thiodipropionate.

8. Peroxide scavengers, for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulphide, pentaerythritol tetrakis-(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, such as talc, metal oxides, such as titanium dioxide or magnesium oxide, phosphates, carbonates or sulphates of, preferably, alkaline earth metals; organic compounds, such as mono- or polycarboxylic acids and their salts, such as 4-t-butylbenzoic acid, adipic acid, diphenyl acetic add, sodium succinate or sodium benzoate; and polymeric compounds, for example ionic copolymers (ionomers).

12. Benzofuranones and indolinones as described, for example, in U.S. Pat. No. 4,325,863; U.S. Pat. No. 4,338,244; U.S. Pat. No. 5,775,312, U.S. Pat. No. 5,216,052; U.S. Pat. No. 5,252,643; DE-A-4 316 611; DE-A-4 316 622; DE-A4 316 876; EP-A-0 589 839 or EP-A-0 591 102, or 3-[4-(2-acetoxyethoxy)phenyl]-5,7-di-t-butylbenzofuran-2-one, 5,7-di-t-butyl-3-[4-(2-stearoyloxyethoxy)phenyl]benzofuran-2-one, 3,3'-bis[5,7-di-t-butyl-3-(4-[2-hydroxyethoxy]phenyl)benzofuran-2-one], 5,7-di-t-butyl-3-(4-ethoxyphenyl)benzofuran-2-one, 3-(4-acetoxy-3,5-dimethylphenyl)-5,7-di-t-butylbenzofuran-2-one, 3-(3,5-dimethyl-4-pivaloyloxyphenyl)-5,7-di-t-butylbenzofuran-2-one, 3-(3,4-dimethylphenyl)-5,7-di-t-butylbenzofuran-2-one, 3-(2,3-dimethylphenyl)-5,7-di-t-butylbenzofuran-2-one.

13. Other additives, for example plasticisers, lubricants, emulsifiers, pigments, rheological additives, catalysts, levelling assistants, optical brighteners, flame proofing agents, antistatic agents or blowing agents.

A specific embodiment of the present invention relates to a new crystal form of pentaerythritol tetrakis[3-(3,5-di-tert-butyl-4-hydroxyphenyl)-propionate]. The new crystal form has a melting point of 123° C. and a characteristic X-ray diffraction pattern, which can be differentiated clearly from other crystal forms, such as the λ-modification as defined in U.S. Pat. No. 4,683,326. The melting point of 123° C. differentiates the new crystal form from other crystal modifications, such as the known β-modification, melting point: 116° C., or the δ-modification: melting point: 118° C.

The new crystal form of pentaerythritol tetrakis[3-(3,5-di-tert-butyl-4-hydroxyphenyl)propionate] is characterised in the X-ray powder diffraction pattern by the interplanar spacings [d-values] and relative line intensities of the following principal lines (CuK radiation: 35 kV, 60 mA, automatic divergence slit, diffracted beam monochromator receiving slit: 0.2 mm, scatter slit: 1°):

| d-spacing [Å] | Relative intensity |
|---|---|
| 22.7 | strong |
| 19.7 | strong |
| 14.9 | medium |
| 13.1 | medium |
| 11.3 | medium |
| 9.0 | weak |
| 8.6 | medium |
| 7.6 | weak |
| 7.1 | very strong |
| 6.6 | weak |
| 5.94 | weak |
| 5.63 | medium |
| 5.45 | weak |
| 5.26 | medium |
| 5.06 | medium |
| 4.82 | medium |
| 4.74 | strong |
| 4.58 | medium |
| 4.43 | very strong |
| 4.30 | weak |
| 4.09 | weak |
| 3.93 | weak |
| 3.75 | weak |

The unit Å The new crystal modification (µ-form) of pentaerythritol tetrakis[3-(3,5-di-tert-butyl-4-hydroxyphenyl)-propionate] is characterised more precisely in the X-ray powder diffraction pattern by the following interplanar spacings [d-values] and relative line intensities including the principal lines and weaker lines:

| d-spacing [Å] | Relative intensity |
|---|---|
| 22.7 | strong |
| 19.7 | strong |
| 14.9 | medium |
| 13.1 | medium |
| 12.4 | very weak |
| 11.3 | medium |
| 10.9 | very weak |
| 9.9 | very weak |
| 9.0 | weak |
| 8.6 | medium |
| 7.6 | weak |
| 7.1 | very strong |
| 6.6 | weak |
| 6.3 | very weak |
| 5.94 | weak |
| 5.81 | very weak |
| 5.63 | medium |
| 5.45 | weak |
| 5.35 | very weak |
| 5.26 | medium |
| 5.06 | medium |
| 4.93 | weak |
| 4.82 | medium |
| 4.74 | strong |
| 4.58 | medium |
| 4.52 | weak |
| 4.43 | very strong |
| 4.30 | weak |
| 4.13 | very weak |
| 4.09 | weak |
| 3.93 | weak |
| 3.75 | weak |
| 3.59 | very weak |
| 3.42 | very weak |
| 3.33 | very weak |
| 3.25 | very weak |
| 3.16 | very weak |
| 3.06 | very weak |

The new crystal form, particularly the novel crystal modification (µ-form) of pentaerythritol tetrakis[3-(3,5-di-tert-butyl hydroxyphenyl)-propionate], is a preferred crystal form of this compound that is advantageous as compared with other crystal forms. For example, the use of the crystal modification (µ-form) of pentaerythritol tetrakis[3-(3,5-di-tert-butyl-4 hydroxyphenyl)-propionate] as seed crystals, in combination with the partial ester of polyoxyethylene sorbitan, particularly polyoxyethylene-(20 or 5)-sorbitan monooleate, in the process for preparing the solid particles defined above, is particularly advantageous, as it assures a rapid and complete crystallisation process.

The present invention also relates to the aqueous dispersion comprising the new crystal form, in particular the crystal modification (µ-form) of pentaerythritol tetrakis[3-(3,5-di-tert-butyl-4-hydroxyphenyl)-propionate].

A further embodiment of the invention relates to the aqueous dispersion comprising the new crystal form, in particular the crystal modification (µ-form) of pentaerythritol tetrakis[3-(3,5-ditert-butyl-4-hydroxyphenyl)-propionate], in admixture with other crystal forms.

The present invention also relates to a process for preparing the crystal form, particularly the modification (µ-form) of pentaerythritol tetrakis[3-(3,5-di-tert-butyl-4-hydroxyphenyl)-propionate] as defined above, which is characterised in that a homogeneous alcoholic aqueous dispersion is prepared comprising pentaerythritol tetrakis[3-(3,5-di-tert-butyl-4-hydroxyphenyl)-propionate] and a lower alcohol selected from the group consisting of ethanol, isopropanol and 2-butanol and crystals are formed by the addition at temperatures above 90° C. of polyoxyethylene-(20 or 5)sorbitan monooleate and seed crystals.

The process comprises the process step of heating a melt or a suspension of pentaerythritol tetrakis[3-(3,5-di-tert-butyl-4-hydroxyphenyl)-propionate] in an aqueous alcoholic solution comprising a lower alcohol selected from the group consisting of ethanol, isopropanol and 2-butanol to a temperature in the range from 90° C. to the boiling point of the dispersion. The dispersion is mixed thoroughly by vigorous stirring. The formation of the crystal form is accelerated by inoculating the aqueous ethanolic solution with crystals of the µ-modification obtained from a previous batch. Crystals of a different modification, such as the λ-modification, as described in U.S. Pat. No. 4,683,326, may also be added in admixture with the crystals of the µ-modification.

The new crystal form is particularly suitable in a process for preparing a batch comprising crystalline pentaerythritol tetrakis[3-(3,5-di-tert-butyl-4-hydroxyphenyl)-propionate]. According to this process an aqueous homogeneous dispersion comprising pentaerythritol tetrakis[3-(3,5-di-tert-butyl-4-hydroxyphenyl)-propionate] is prepared, polyoxyethylene-(20 or 5)-sorbitan monooleate is added and the dispersion is seeded with crystals of the crystal modification (µ-form) in optional admixture with other crystal forms.

Another specific embodiment of the present invention relates to a new crystal form of N,N'-hexane-1,6-diyl-bis[3-(3,5-di-tert-butyl-4-hydroxyphenylpropionamide)]. The new crystal form has a characteristic X-ray diffraction pattern, which can be differentiated clearly from other crystal forms, such as the α-modification, which is obtainable from the solvent toluene by known process methods.

Such known process method for obtaining crystals of the α-modification of N,N'-hexane-1,6-diyl-bis[3-(3,5-di-tert-butyl-4-hydroxyphenylpropionamide)] is described as follows:

1580 ml toluene is added to a 5 l double jacket reactor equipped with a condenser, an anchor stirrer and a transfer tube, which is heated to 110° C. (stirrer speed 150 rpm). 890 g N,N'-hexane-1,6-diyl-bis[3-(3,5-di-tert-butyl-4-hydroxyphenylpropionamide)] dissolved in 1200 ml toluene are added at 90° C. The transfer tube is rinsed with 250 ml toluene. After heating the solution to 80° C. 0.1 g crystalline N,N'-hexane-1,6-diyl-bis[3-(3,5-di-tert-butyl-4-hydroxyphenylpropionamide)] is added as seed material. The solution is cooled to 77° C. and kept at this temperature for 60 minutes. The solution is then cooled to 20° C. and kept at this temperature for another 60 minutes. The crystalline suspension is filtered and washed three times with 3120 ml toluene. The white crystals are dried for 24 h in the vacuum at 40 mbar.

The crystal modification (α-form) of N,N'-hexane-1,6-diyl-bis[3-(3,5-di-tert-butyl-4-hydroxyphenylpropionamide)] is characterised more-precisely in the X-ray powder diffraction pattern by the following interplanar spacings [d-values] and relative line intensities including the principal lines and weaker lines:

| d-spacing [Å] | Relative intensity |
|---|---|
| 16.0 | medium |
| 13.8 | very weak |
| 12.7 | weak |
| 10.5 | very strong |
| 8.5 | medium |
| 8.0 | medium |
| 7.5 | medium |
| 6.9 | medium |
| 6.8 | medium |
| 6.3 | weak |
| 6.1 | medium |
| 5.83 | weak |
| 5.60 | medium |
| 5.25 | strong |
| 4.99 | strong |
| 4.71 | strong |
| 4.60 | strong |
| 4.37 | strong |
| 4.23 | medium |
| 4.03 | weak |
| 3.85 | weak |
| 3.75 | very weak |
| 3.63 | very weak |
| 3.54 | weak |
| 3.49 | medium |
| 3.38 | very weak |
| 3.29 | weak |
| 3.25 | weak |
| 3.18 | very weak |
| 3.13 | very weak |
| 3.04 | weak |

The new crystal form of N,N'-hexane-1,6-diyl-bis[3-(3,5-di-tert-butyl-4-hydroxyphenylpropionamide)] is characterised in the X-ray powder diffraction pattern by the interplanar spacings [d-values] and relative line intensities of the following principal lines (CuK radiation: 35 kV, 60 mA, automatic divergence slit, diffracted beam monochromator receiving slit: 0.2 mm, scatter slit: 1°):

| d-spacing [Å] | Relative intensity |
|---|---|
| 7.3 | medium |
| 5.13 | strong |
| 4.88 | medium |
| 3.92 | weak |

The new crystal form of N,N'-hexane-1,6-diyl-bis[3-(3,5-di-tert-butyl-4-hydroxyphenylpropionamide)] is characterised more precisely in the X-ray powder diffraction pattern by the following interplanar spacings [d-values] and relative line intensities including the principal lines and weaker lines:

| d-spacing [Å] | Relative intensity |
|---|---|
| 11.1 | weak |
| 10.3 | medium |
| 7.9 | medium |
| 7.3 | medium |
| 5.13 | strong |
| 5.06 | strong |
| 4.88 | medium |
| 3.92 | weak |

The new crystal modification (β-form) of N,N'-hexane-1,6-diyl-bis[3-(3,5-di-tert-butyl-4-hydroxyphenylpropionamide)] is characterised more precisely in the X-ray powder diffraction pattern by the following interplanar spacings [d-values] and relative line intensities including the principal lines and weaker lines:

| d-spacing [Å] | Relative intensity |
|---|---|
| 16.0 | very weak |
| 13.6 | very weak |
| 12.7 | very weak |
| 11.1 | weak |
| 10.5 | medium |
| 10.3 | medium |
| 9.1 | very weak |
| 8.5 | weak |
| 8.0 | medium |
| 7.9 | medium |
| 7.5 | medium |
| 7.3 | medium |
| 7.1 | medium |
| 6.8 | weak |
| 6.4 | weak |
| 6.2 | medium |
| 6.1 | medium |
| 5.94 | weak |
| 5.83 | very weak |
| 5.58 | medium |
| 5.24 | medium |
| 5.13 | strong |
| 5.06 | strong |
| 4.98 | medium |
| 4.88 | medium |
| 4.71 | medium |
| 4.59 | strong |
| 4.54 | strong |
| 4.38 | strong |
| 4.24 | medium |
| 4.13 | medium |
| 3.92 | weak |
| 3.85 | weak |
| 3.70 | very weak |
| 3.53 | weak |
| 3.38 | very weak |
| 3.29 | very weak |
| 3.05 | very weak |

The new crystal form, particularly the novel crystal modification (β-form) of N,N'-hexane-1,6-diyl-bis[3-3,5-di-tert-butyl hydroxyphenylpropionamide)], is a preferred crystal form of this compound that is advantageous as compared with other crystal forms. For example, the use of the crystal modification (β-form) of N,N'-hexane-1,6-diyl-bis[3-(3,5-di-tert-butyl-4-hydroxyphenylpropionamide)] as seed crystals, in combination with the partial ester of polyoxyethylene sorbitan, particularly polyoxyethylene-(20 or 5)-sorbitan monooleate, in the process for preparing the solid particles defined above, is particularly advantageous, as it assures a rapid and complete crystallisation process.

The present invention also relates to the aqueous dispersion comprising the new crystal form, in particular the crystal modification (β-form) of N,N'-hexane-1,6-diyl-bis[3-(3,5-di-tert-butyl-4-hydroxyphenylpropionamide)].

A further embodiment of the invention relates to the aqueous dispersion comprising the new crystal form, in particular the crystal modification (β-form) of N,N'-hexane-1,6-diyl-bis[3-(3,5-di-tert-butyl-4-hydroxyphenylpropionamide)] in admixture with other crystal forms.

The present invention also relates to a process for preparing the crystal form, particularly the crystal modification (β-form) of N,N'-hexane-1,6-diyl-bis[3-(3,5-di-tert-butyl-4-hydroxyphenylpropionamide)] as defined above, which is characterised in that a homogeneous aqueous or alcoholic aqueous dispersion is prepared comprising N,N'-hexane-1,6-diyl-bis[3-(3,5-di-tert-butyl-4-hydroxyphenylpropionamide)] and optionally a lower alcohol selected from the group consisting of ethanol, isopropanol and 2-butanol and crystals are formed by the addition at temperatures above 75° C. of polyoxyethylene-(20 or 5)-sorbitan monooleate and seed crystals.

The process comprises the process step of heating a melt or a suspension of N,N'-hexane-1,6-diyl-bis[3-(3,5-di-tert-butyl hydroxyphenylpropionamide)] (β-form) in water or an aqueous alcoholic solution comprising a lower alcohol selected from the group consisting of ethanol, isopropanol and 2-butanol at a temperature above 75° C. to the boiling point of the dispersion, preferably in the range from 75° C.–90° C. The dispersion is mixed thoroughly by vigorous stirring. The formation of the crystal form is accelerated by inoculating the aqueous ethanolic solution with crystals of the β-modification obtained from a previous batch.

The new crystal form is particularly suitable in a process for preparing a batch comprising crystalline N,N'-hexane-1,6-diyl-bis[3-(3,5-di-tert-butyl hydroxyphenylpropionamide)]. According to this process, an aqueous homogeneous dispersion comprising N,N'-hexane-1,6-diyl-bis[3-(3,5-di-tert-butyl-4-hydroxyphenylpropionamide)] (β-form) is prepared, polyoxyethylene-(20 or 5)-sorbitan monooleate is added and the dispersion is seeded with crystals of the crystal modification (β-form) in optional admixture with other crystal forms.

A further embodiment of the invention relates to the further processing of the aqueous dispersion defined above comprising the crystal modifications of pentaerythritol tetrakis[3-(3,5-di-tert-butyl-4-hydroxyphenyl)-propionate] (µ-form) and/or N,N'-hexane-1,6-diyl-bis[3-(3,5-di-tert-butyl-4-hydroxyphenylpropionamide)] (β-form). That dispersion is particularly suitable for stabilising organic material, especially polymers, specifically styrene (co)polymers, such as polystyrene, ABS (acrylonitrile-butadiene-styrene), IPS (impact polystyrene, graft copolymer of styrene on polybutadiene), MBS (methacrylonitrile-butadiene-styrene) and SBS (styrene-butadiene-styrene). Another embodiment of the invention relates to polymer compositions comprising a') The aqueous dispersion defined above comprising the crystal modifications of pentaerythritol tetrakis[3-(3,5-di-tert-butyl-4-hydroxyphenyl)-propionate] (µ-form) and/or N,N'-hexane-1,6-diyl-bis[3-(3,5-di-tert-butyl-4-hydroxyphenylpropionamide)] (β-form) and, optionally further additives;

b') The polymer material to be stabilised against oxidative, thermal or light-induced degradation.

The incorporation into the polymer materials can be carried out, for example, by mixing in the composition and, if desired, further additives in accordance with known methods. The incorporation into the polymeric material may take place prior to or during the shaping operation or by applying the composition to the polymer, with or without subsequent evaporation of the solvent. In the case of elastomers, these can also be stabilised as lattices. The invention therefore relates in particular to compositions, wherein the dispersion defined above is incorporated into and/or chemically linked with an elastomer/polymer.

The aqueous dispersion can also be added in the form of a master batch, which contains the individual components defined above in a concentration, for example from 2.5 to 25.0% by weight, to the polymer material which is to be stabilised.

The dispersion defined above can be incorporated into polymers by the following methods:

As emulsion or dispersion (e.g. to lattices or emulsion polymers);

As a dry mix during the mixing in of additional components or polymer mixtures;

By direct addition to the processing apparatus (e.g. extruder, internal mixer, etc.);

As a solution or melt.

Therefore, the present invention also relates to the process for the preparation of the polymer composition, which comprises incorporating within the polymer material to be stabilised against oxidative, thermal or light-induced degradation the aqueous dispersion defined above.

The polymer compositions can be employed in various forms and processed to give various products, for example as or to films, fibres, tapes, moulding compounds or profiles, or as binders for coating materials, adhesives or putties. The following examples illustrate the invention:

EXAMPLES

Example 1

1.1 Standard Procedure

The process for the preparation of solid particles is carried out in a 3 l double jacket reactor, equipped with an Ekato Intermig stirrer, an inlet for the melt and a thermometer. The melt is prepared in an additional 1 l double jacket reactor, which is equipped with an anchor stirrer and connected with the other reactor through a glass pipe. Both steps, the preparation of the melt and the solid particles, are carried out under a nitrogen atmosphere.

Water (200% by weight, based on the melt), the surfactant TWEEN 80 and a batch of seed crystals are mixed in the 3 l reactor and heated to the temperature of forming the solid particles. The melt is added at a rate of 300 to 360 g/h and the temperature is maintained at the given temperature. The suspension formed is then stirred for an additional 30 min. after the dosing. After cooling to 50° C. the granules are filtered off and washed with water. The particles are subsequently dried in the vacuum.

1.2 The standard procedure is applied and solid particles are obtained by adding a melt of 900 g IRGANOX 1098 to 1800 g water at 95° C., which contains 4.5 g TWEEN 80 (0.5%) and 70 g IRGANOX 1098 (7.8%) seed crystals. The temperature of the melt is 180° C.

1.3 The standard procedure is applied and a mixture of IRGANOX 1010 with IRGAFOS 168 is obtained in solid particles by adding a melt of 297 g IRGANOX 1010 and 603 g IRGAFOS 168 (=900 g IRGANOX B215) to an aqueous phase that contains 70 g (7.8%) IRGANOX B215 seed crystals and 4.5 g TWEEN 80 (0.5%).

1.4 The standard procedure is applied and IRGANOX 1010 is obtained in solid particles by adding 900 g of the melt to an aqueous phase that contains 70 g (7.8%) IRGANOX 1010 seed crystals and 2.0 g TWEEN 80.

1.5 The standard procedure is applied and solid particles of the μ-crystal form are obtained by adding a melt of 300 g IRGANOX 1010 to a mixture of 540 g water and 60 g ethanol at 90° C., which contains 1.5 g TWEEN 80 (0.5%) and 15 g IRGANOX 1010 (5.0%) seed crystals of the μ-crystal form. The temperature of the melt is 140° C.

1.6 The standard procedure is applied and solid particles of the μ-crystal form are obtained by adding a melt of 300 g IRGANOX 1010 to a mixture of 600 g water and 60 g 2-propanol at 90° C., which contains 1.5 g TWEEN 80 (0.5%) and 15 g IRGANOX 1010 (5.0%) seed crystals of the μ-crystal form. The temperature of the melt is 140° C.

1.7 The standard procedure is applied and solid particles of the μ-crystal form are obtained by adding a melt of 300 g IRGANOX 1010 to a mixture of 600 g water and 60 g 2-butanol at 90° C., which contains 0.5 g TWEEN 80 (0.16%) and 3.8 g IRGANOX 1010 (1.3%) seed crystals of the μ-crystal form. The temperature of the melt is 140° C.

1.8 The standard procedure is applied and solid particles of the β-form are obtained by adding a melt of 900 g IRGANOX 1098 to 1800 g water at 95° C., which contains 0.9 g TWEEN 80 (0.1%) and 70 g IRGANOX 1098 (7.8% h) seed crystals. The temperature of the melt is 180° C.

Example 2

917 g Water, 3 g TWEEN 80 and a batch of 80 g seed crystals (50μ) of IRGANOX 1010 are mixed in a 3 l reactor and heated up to 90° C. 200 g amorphous IRGANOX 1010, preferably in spherical shape are added. The suspension formed is then stirred at 90° C. and 190 rpm for an additional hour. After cooling to room temperature the crystals are filtered off and washed with water. The crystals are subsequently dried in the vacuum.

The invention claimed is:

1. A process for preparing solid particles comprising in essentially crystalline form a compound of the formula:

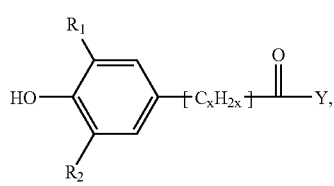

(I)

wherein
one of $R_1$ and $R_2$ independently of one another represents hydrogen or $C_1$–$C_4$alkyl and the other one represents $C_3$–$C_4$alkyl;
x represents zero (direct bond) or a numeral from one to three; and
Y represents $C_8$–$C_{22}$alkoxy; or groups of the partial formulae

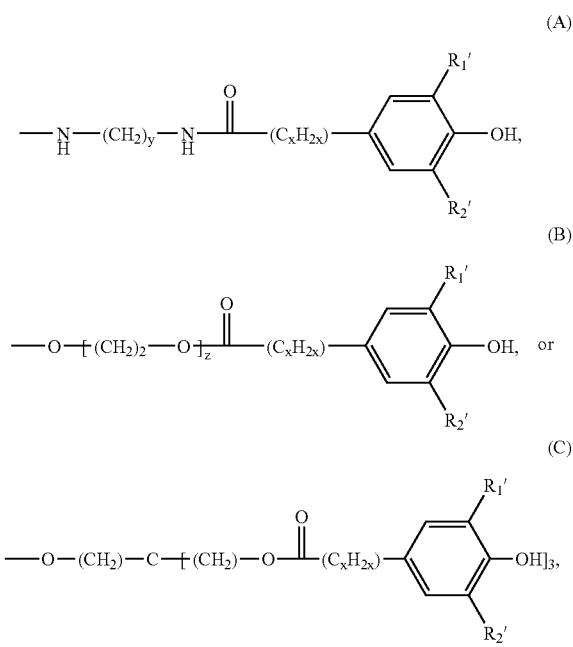

wherein
one of $R_1'$ and $R_2'$ independently of one another represents hydrogen or $C_1$–$C_4$alkyl and the other one represents $C_3$–$C_4$alkyl;
x represents zero (direct bond) or a numeral from one to three;
y represents a numeral from two to ten: and
z represents a numeral from two to six,
characterised in that a homogeneous aqueous dispersion is prepared, which comprises the compound (I) or a mixture thereof, wherein $R_1$, $R_2$, $R_1'$, $R_2'$, Y, x, y and z are as defined above, crystals are formed by the addition of a fatty acid partial ester of polyoxyethylene sorbitan and seed crystals and the crystals obtained are separated from the dispersion.

2. A process step of further processing the solid particles comprising in essentially crystalline form the compound (I), characterised in that a homogeneous aqueous dispersion is prepared, which comprises the compound (I) or a mixture thereof, wherein $R_1$, $R_2$, $R_1'$, $R_2'$, Y, x, y and z are as defined in claim 1, crystals are formed by the addition of a fatty acid partial ester of polyoxyethylene sorbitan and seed crystals and the crystals obtained are separated from the dispersion and further processed to other solid particle forms.

3. A process according to claim 1, characterised in that crystals are formed by the addition of a fatty acid partial ester of polyoxyethylene sorbitan selected from the group consisting of polyoxyethylene sorbitan polyoxyethylene(20 or 4)-sorbitan monolaurate, polyoxyethylene-(20)-sorbitan monopalmitate or monostearate, polyoxyethylene-(4 or 20)-sorbitan monostearate or tristearate, polyoxyethylene-(20 or 5)-sorbitan monooleate and polyoxyethylene-(20)-sorbitan trioleate.

4. A process according to claim 3, characterised in that the crystals are formed by the addition of polyoxyethylene-(20 or 5)-sorbitan monooleate.

5. A process according to claim 1 for preparing solid particles comprising in essentially crystalline form a compound (I) or a mixture thereof, wherein one of $R_1$ and $R_2$ independently of one another represents hydrogen or tert-butyl and the other one represents tert-butyl;

x represents two; and

Y represents $C_8$–$C_{22}$alkoxy; or groups of the partial formulae (A), (B) or (C), wherein one of $R_1'$ and $R_2'$ independently of one another represents hydrogen or tert-butyl and the other one represents tert-butyl;

x represents two; y represents six; and z represents three, characterised in that the crystals are formed by the addition of polyoxyethylene-(20 or 5)-sorbitan monooleate.

6. A process according to claim 2, characterised in that the crystals obtained are separated from the dispersion and converted to granulates.

7. Compressed article comprising a compound (I) or a mixture thereof in essentially crystalline form obtainable by the process according to claim 2.

8. An aqueous dispersion comprising
a) In essentially crystalline form a compound (I) or a mixture thereof, wherein $R_1$, $R_2$, $R_1'$, $R_2'$, Y, x, y and z are as defined in claim 1;
b) A fatty acid partial ester of polyoxyethylene sorbitan; and
c) Water.

9. An aqueous dispersion according to claim 1 comprising as component a) in essentially crystalline form pentaerythritol tetrakis[3-(3,5-di-tert-butyl-4-hydroxyphenyl)-propionate].

10. An aqueous dispersion according to claim 1 comprising as component a) in essentially crystalline form N,N'-hexane-1,6-diyl-bis[3-3,5-di-tert-butyl-4-hydroxyphenyl-propionamide)].

11. A crystal form of pentaerythritol tetrakis[3-(3,5-di-tert-butyl-4-hydroxyphenyl)-propionate] characterised in the X-ray powder diffraction pattern by the interplanar spacings [d-values] and relative line intensities of the following principal lines:

| d-spacing [Å] | Relative intensity |
|---|---|
| 22.7 | strong |
| 19.7 | strong |
| 14.9 | medium |
| 13.1 | medium |
| 11.3 | medium |
| 9.0 | weak |
| 8.6 | medium |
| 7.6 | weak |
| 7.1 | very strong |
| 6.6 | weak |
| 5.94 | weak |
| 5.63 | medium |
| 5.45 | weak |
| 5.26 | medium |
| 5.06 | medium |
| 4.82 | medium |
| 4.74 | strong |
| 4.58 | medium |
| 4.43 | very strong |
| 4.30 | weak |
| 4.09 | weak |
| 3.93 | weak |
| 3.75 | weak. |

12. A crystal modification (μ-form) of pentaerythritol tetrakis[3-(3,5-di-tert-butyl-4-hydroxyphenyl)-propionate] according to claim 11, characterised in the X-ray powder diffraction pattern by the interplanar spacings [d-values] and relative line intensities:

| d-spacing [Å] | Relative intensity |
|---|---|
| 22.7 | strong |
| 19.7 | strong |
| 14.9 | medium |
| 13.1 | medium |
| 12.4 | very weak |
| 11.3 | medium |
| 10.9 | very weak |
| 9.9 | very weak |
| 9.0 | weak |
| 8.6 | medium |
| 7.6 | weak |
| 7.1 | very strong |
| 6.6 | weak |
| 6.3 | very weak |
| 5.94 | weak |
| 5.81 | very weak |
| 5.63 | medium |
| 5.45 | weak |
| 5.35 | very weak |
| 5.26 | medium |
| 5.06 | medium |
| 4.93 | weak |
| 4.82 | medium |
| 4.74 | strong |
| 4.58 | medium |
| 4.52 | weak |
| 4.43 | very strong |
| 4.30 | weak |
| 4.13 | very weak |
| 4.09 | weak |
| 3.93 | weak |
| 3.75 | weak |
| 3.59 | very weak |
| 3.42 | very weak |
| 3.33 | very weak |
| 3.25 | very weak |
| 3.16 | very weak |
| 3.06 | very weak. |

13. An aqueous dispersion comprising the crystal modification (μ-form) of pentaerythritol tetrakis[3-3,5-di-tert-butyl-4-hydroxyphenyl)-propionate] as defined in claim 12.

14. A crystal form of N,N'-hexane-1,6-diyl-bis[3-(3,5-di-tert-butyl-4-hydroxyphenylpropionamide)] characterised in the X-ray powder diffraction pattern by the interplanar spacings [d-values] and relative line intensities of the principal lines:

| d-spacing [Å] | Relative intensity |
|---|---|
| 7.3 | medium |
| 5.13 | strong |
| 4.88 | medium |
| 3.92 | weak. |

15. A crystal form of N,N'-hexane-1,6-diyl-bis[3-(3,5-di-tert-butyl-4-hydroxyphenylpropionamide)] according to claim 14, characterised in the X-ray powder diffraction pattern by the interplanar spacings [d-values] and relative line intensities including the principal lines and weaker lines:

| d-spacing [Å] | Relative intensity |
|---|---|
| 11.1 | weak |
| 10.3 | medium |
| 7.9 | medium |
| 7.3 | medium |
| 5.13 | strong |
| 5.06 | strong |
| 4.88 | medium |
| 3.92 | weak. |

16. A crystal modification (β-form) of N,N'-hexane-1,6-diyl-bis[3-(3,5-di-tert-butyl-4-hydroxyphenylpropionamide)] characterised in the X-ray powder diffraction pattern by the following interplanar spacings [d-values] and relative line intensities including the principal lines and weaker lines:

| d-spacing [Å] | Relative intensity |
|---|---|
| 16.0 | very weak |
| 13.6 | very weak |
| 12.7 | very weak |
| 11.1 | weak |
| 10.5 | medium |
| 10.3 | medium |
| 9.1 | very weak |
| 8.5 | weak |
| 8.0 | medium |
| 7.9 | medium |
| 7.5 | medium |
| 7.3 | medium |
| 7.1 | medium |
| 6.8 | weak |
| 6.4 | weak |
| 6.2 | medium |
| 6.1 | medium |
| 5.94 | weak |
| 5.83 | very weak |
| 5.58 | medium |
| 5.24 | medium |
| 5.13 | strong |
| 5.06 | strong |
| 4.98 | medium |
| 4.88 | medium |
| 4.71 | medium |
| 4.59 | strong |
| 4.54 | strong |
| 4.38 | strong |
| 4.24 | medium |
| 4.13 | medium |
| 3.92 | weak |
| 3.85 | weak |
| 3.71 | very weak |
| 3.53 | weak |
| 3.38 | very weak |
| 3.29 | very weak |
| 3.05 | very weak. |

17. An aqueous dispersion comprising the crystal modification (β-form) of N,N'-hexane-1,6-diyl-bis[3-(3,5-di-tert-butyl-4-hydroxyphenylpropionamide)] as defined in claim 16.

* * * * *

UNITED STATES PATENT AND TRADEMARK OFFICE
CERTIFICATE OF CORRECTION

| | | |
|---|---|---|
| PATENT NO. | : 7,262,319 B2 | Page 1 of 1 |
| APPLICATION NO. | : 10/534513 | |
| DATED | : August 28, 2007 | |
| INVENTOR(S) | : Daniel Rehm et al. | |

It is certified that error appears in the above-identified patent and that said Letters Patent is hereby corrected as shown below:

Title page

Item (87) should read:

-- (87) PCT Pub. No.:    WO2004/048312

PCT Pub. Date:  Jun. 10, 2004 --.

Signed and Sealed this

Twentieth Day of November, 2007

JON W. DUDAS
*Director of the United States Patent and Trademark Office*